US00PP25498P3

(12) United States Plant Patent
Olesen

(10) Patent No.: US PP25,498 P3
(45) Date of Patent: May 5, 2015

(54) MINIATURE ROSE PLANT NAMED 'POULTY018'

(50) Latin Name: ***Rosa* hybrid**
Varietal Denomination: Poulty018

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 13/986,936

(22) Filed: Jun. 14, 2013

(65) Prior Publication Data

US 2014/0373221 P1 Dec. 18, 2014

(51) Int. Cl.
*A01H 5/00* (2006.01)

(52) U.S. Cl.
USPC ..... Plt./122

(58) Field of Classification Search
USPC ..... Plt./122, 129
See application file for complete search history.

*Primary Examiner* — Kent L Bell

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

3 Drawing Sheets

Botanical designation: *Rosa* hybrid.
Variety denomination: 'Poulty018'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulty018', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty018' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty018' was selected by the inventor as a single plant from the progeny of the hybridization in 2007.

Asexual reproduction of 'Poulty018' by cuttings was first done by Mogens N. Olesen in the nursery in Fredensborg, Denmark in 2008. This initial and other subsequent propagations conducted in controlled environments have demonstrated that the characteristics of 'Poulty018' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty018'.

Specifically illustrated in FIG. 1 are the flower at various stages of development and flower parts.

Figure 2:
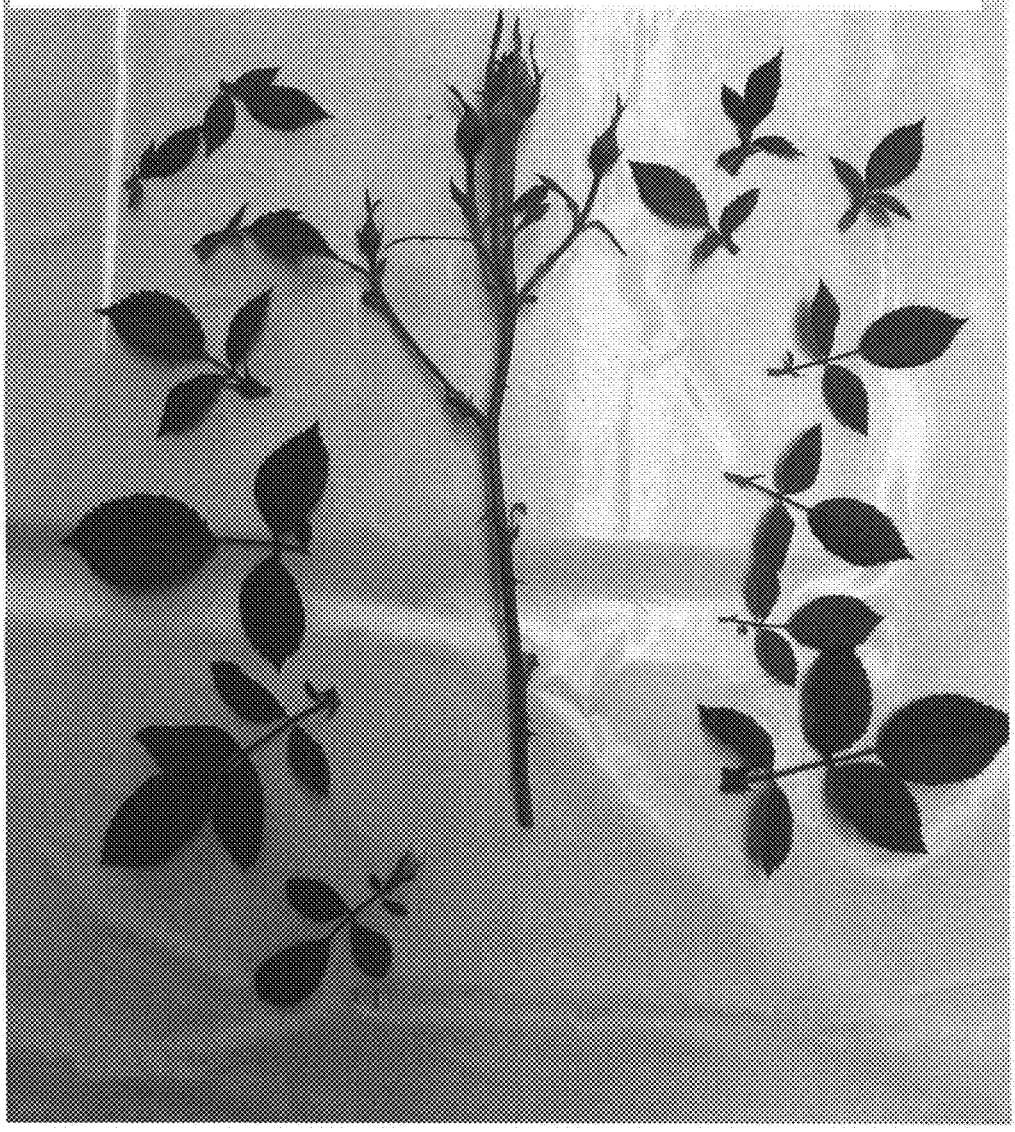

Specifically illustrated in FIG. 2 are the leaves and stems.

Figure 3:
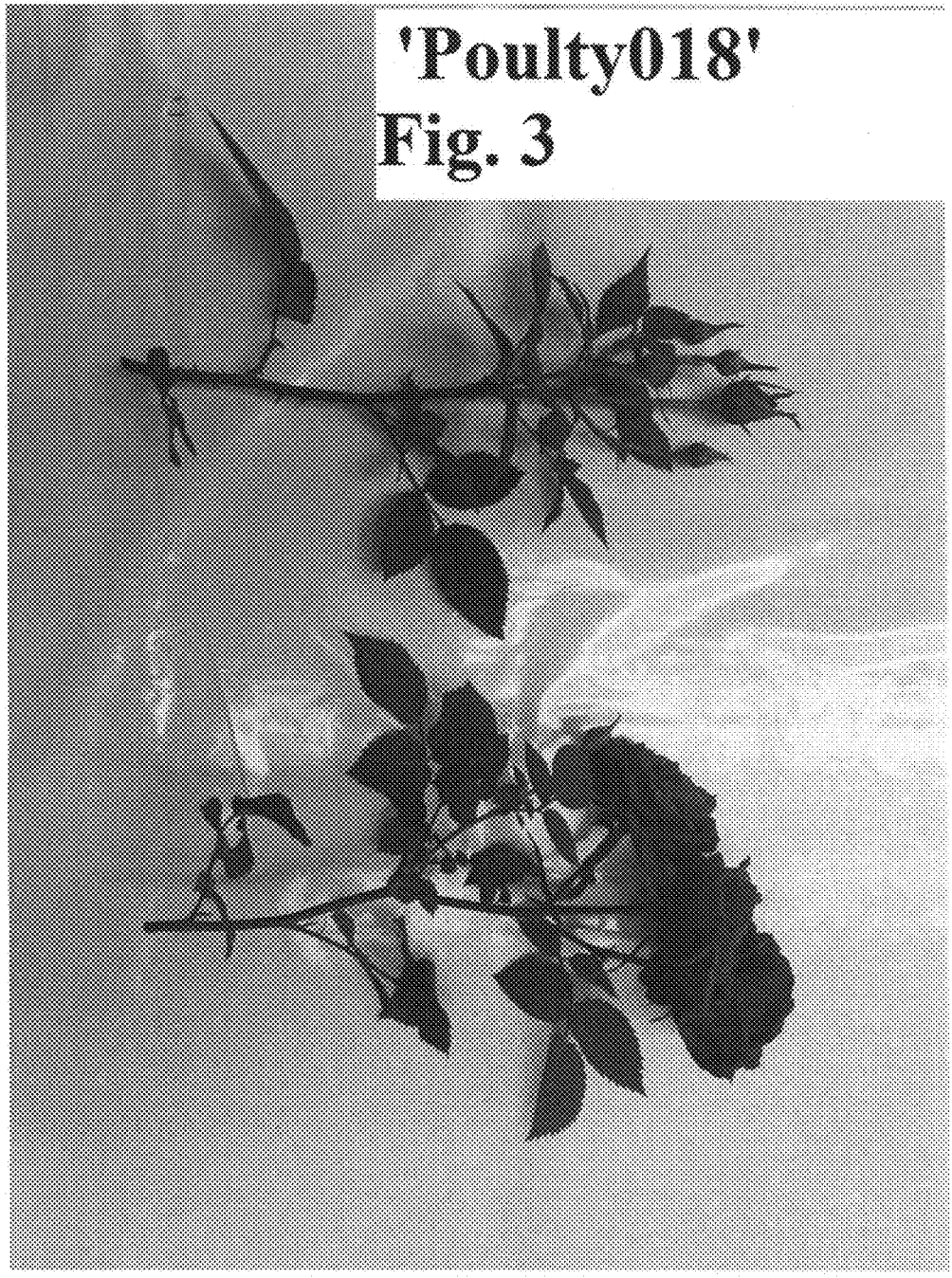

Specifically illustrated in FIG. 3 are stems showing attachment of leaves, flower buds, and open flowers.

DETAILED DESCRIPTION OF THE VARIETY

The following is a description of 'Poulty018', as observed in its growth in glasshouses in Fredensborg, Denmark. Observed plants are 3 months of age and were cultivated in 20 cm pots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148 are compared to 'Poulty018' in Chart 1.

CHART 1

| | 'Poulty018' | 'Poulpar029' |
|---|---|---|
| Petalage: | 40 petals | 30 petals |
| Flower Diameter: | 45 to 55 mm | 35 mm |
| General Tonality of Flower Color: | Red Group 46A | Red Group 53A |

FLOWER AND FLOWER BUD

Blooming habit: Continuous.

Flower bud:

*Size*.—Upon opening, 25 mm in length from base of receptacle to end of bud. 10 mm in diameter.

*Bud form*.—Ovate.

*Bud color*.—As sepals unfold, petals are Red-Purple Group 60A.

*Sepals*.—Upper Surface: Color: Green Group 143C. Texture: Smooth, moderately pubescent. Lower Surface: Color: Yellow Green Group 144A. Texture: Smooth. Shape: Apex: Cirrhose. Base: Flat at union with receptacle. Margins: Margins have weak foliaceous appendages on three of the five sepals and have fine pubescence. Size: 20 mm long by 6 mm wide.

*Receptacle*.—Surface Texture: Smooth. Shape: Campanulate. Size: 5 mm tall and 6 mm wide. Color: Yellow Green Group 144D.

*Pedicel*.—Surface: Smooth. Length: 30 to 40 mm. Diameter: Generally 2.5 mm. Color: Yellow-Green Group 144A. Strength: Medium strength.

*Peduncles*.—Surface: Smooth. Length: About 45 mm. Diameter: Generally 3 mm. Color: Yellow-Green Group 144A.

*Borne*.—Singly and or clusters of 3 to 5 flower buds per branch.

Flower bloom:

*Fragrance*.—Light floral scent.

*Duration*.—As a pot plant, flowers last up to 20 days.

*Size*.—Flower diameter is 45 to 55 mm when open. Flower depth is 20 mm.

*Form*.—General shape is a rosette with many slightly overlapping petals.

*Shape of flower, side view*.—The upper portion is flat. The lower portion is a flattened convex.

Petalage: Under normal conditions, flowers have an average of 40 petals total, 10 of which are petaloids.

Color:

*General tonality*.—Red Group 46A.

*Petals, upon & after opening*.—Outermost and innermost petals are Red Group 46A on the upper surface. Red-Purple Group 60A on the lower surface. At the base of the petal, the upper surface is Yellow Group 10A, and the lower surface is Yellow-Green Group 150D.

Petals:

*Petal reflex*.—Strong.

*Margin*.—Entire, with weak undulations.

*Shape*.—Generally broad and elliptic. Apex shape: Rounded. Base shape: Rounded.

*Size*.—25 mm (l) by 25 mm (w).

*Texture*.—Smooth.

*Thickness*.—Average.

Petaloids:

*Quantity*.—10 on average.

*Shape*.—Irregular, and asymmetric. The apex is rounded and base is acute.

*Color*.—Red Group 46A on the upper surface. Red-Purple Group 60A on the lower surface. At the base of the petaloid, the upper surface is Yellow Group 10A, and the lower surface is Yellow-Green Group 150D.

*Size*.—15 mm (l) by 10 mm (w).

Reproductive organs:

*Pollen*.—None Observed.

*Anthers*.—Size: 1 mm long. Color: Greyed-Brown Group 199A. Quantity: 120 on average.

*Filaments*.—Color: Yellow-Orange Group 14B. Length: About 3 mm.

*Pistils*.—Length: About 4 mm long. Quantity: 20 on average.

*Stigmas*.—Inferior relative to the length of the filaments and the height of the anthers. Color: Orange-Red Group 32B.

*Styles*.—Color: Yellow-Orange Group 23B.

*Seed formation*.—Not observed.

PLANT

Plant growth: Upright. Plants are about 25 cm in height, and 20 cm wide.

Stems:

*Color*.—Juvenile growth: Yellow-Green Group 144A. Mature growth: Yellow-Green Group 144A.

*Length*.—Canes are 15 to 20 cm from the base of the plant to the flowering portion.

*Diameter*.—3 mm.

*Internodes*.—On mature canes, there is an average distance of 30 mm between nodes.

*Surface texture*.—Young and mature wood is smooth.

Prickles:

*Incidence*.—About 8 per 10 cm of stem.

*Size*.—Average length: 5 mm.

*Color*.—Juvenile and mature prickles are Red-Purple Group 70D.

*Shape*.—Concave.

Plant foliage:

*Compound leaf size*.—40 to 80 mm (l) by 40 to 60 mm (w).

*Quantity*.—3 leaves per 10 cm of stem.

*Color of juvenile foliage*.—Upper Leaf Surface: Yellow-Green Group 146A. Lower Leaf Surface: Green Group 138B. Anthocyanin: Greyed-Purple Group generalized on the leaflet.

*Color of mature foliage*.—Upper Leaf Surface: Yellow-Green Group 147A. Lower Leaf Surface: Green Group 138B.

Plant leaves and leaflets:

*Stipules*.—Size: About 10 mm in length. Shape: Linear, slightly broad based with outward extending apecies. Margins: Finely serrated with many stipitate glands. Color: Yellow-Green Group 146B.

*Petiole*.—Length: 10 mm on average. Diameter: About 1 mm. Upper surface: Yellow-Green Group 146A. Lower surface: Yellow-Green Group 144A.

*Rachis*.—Length: 15 mm on average. Diameter: About 1 mm. Upper surface: Yellow-Green Group 146A. Lower surface: Yellow-Green Group 144A.

*Leaflet*.—Number of leaflets: 5 to 7 on normal leaves in middle of the stem. Size: 20 to 35 mm in length by 15 to 20 mm wide. Margin: Doubly serrate and serrate. General Shape: Elliptical. Apex Shape: Mucronate. Base Shape: Round. Texture: Somewhat rough. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulty018', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

Figure 1:
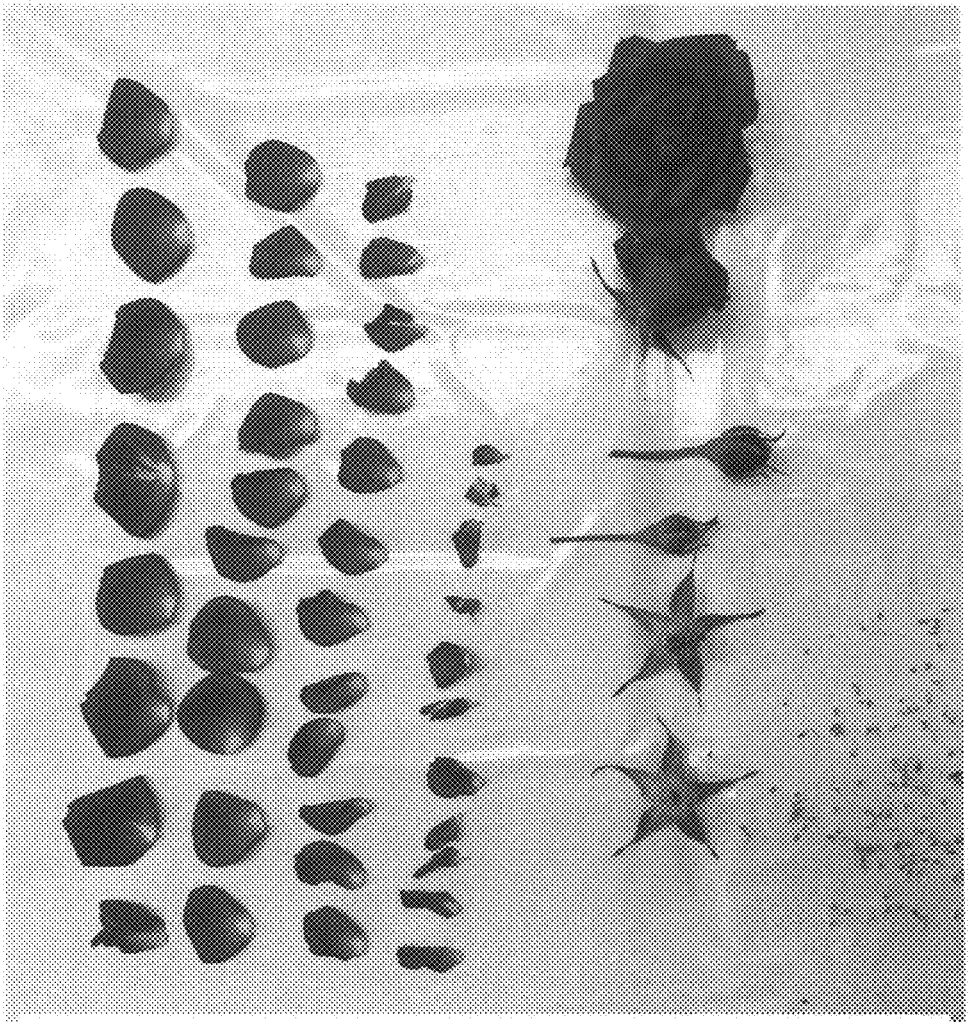

'Poulty018' Fig. 1

'Poulty018' Fig. 2

'Poulty018'